US011278616B2

(12) United States Patent
Matsushita et al.

(10) Patent No.: US 11,278,616 B2
(45) Date of Patent: Mar. 22, 2022

(54) IMMUNITY INDUCTION PROMOTING COMPOSITION, AND VACCINE PHARMACEUTICAL COMPOSITION (71) Applicant: NITTO DENKO CORPORATION, Osaka (JP)

(72) Inventors: Kyohei Matsushita, Osaka (JP); Daisuke Asari, Osaka (JP); Takuya Shishido, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 206 days.

(21) Appl. No.: 15/932,118

(22) PCT Filed: Aug. 3, 2016

(86) PCT No.: PCT/JP2016/072797
§ 371 (c)(1),
(2) Date: Feb. 6, 2018

(87) PCT Pub. No.: WO2017/022793
PCT Pub. Date: Feb. 9, 2017

(65) Prior Publication Data
US 2018/0169227 A1 Jun. 21, 2018

(30) Foreign Application Priority Data
Aug. 6, 2015 (JP) .............................. JP2015-156171

(51) Int. Cl.
A61K 39/00 (2006.01)
A61K 39/39 (2006.01)
A61K 45/00 (2006.01)
A61P 37/04 (2006.01)
A61K 9/00 (2006.01)

(52) U.S. Cl.
CPC ............ *A61K 39/39* (2013.01); *A61K 9/0019* (2013.01); *A61K 39/00* (2013.01); *A61K 45/00* (2013.01); *A61P 37/04* (2018.01); *A61K 2039/55511* (2013.01)

(58) Field of Classification Search
CPC ........ A61K 39/00; A61K 39/39; A61K 45/00; A61K 2039/55511; A61P 37/04
USPC ..................... 424/184.1, 234.1, 278.1, 282.1
See application file for complete search history.

(56) References Cited

U.S. PATENT DOCUMENTS

| | | | | |
|---|---|---|---|---|
| 5,049,389 A | * | 9/1991 | Radhakrishnan .... | A61K 9/1272 424/450 |
| 6,720,001 B2 | * | 4/2004 | Chen .................... | A61K 31/355 424/455 |
| 6,740,325 B1 | | 5/2004 | Arnon et al. | |
| 2007/0141086 A1 | * | 6/2007 | Ohara .................. | A61K 31/545 424/248.1 |
| 2007/0141096 A1 | * | 6/2007 | Van Lengerich ..... | A23L 29/065 424/401 |
| 2008/0112974 A1 | | 5/2008 | Czerkinsky et al. | |
| 2008/0193487 A1 | | 8/2008 | Schild et al. | |
| 2013/0023491 A1 | | 1/2013 | Annes et al. | |
| 2014/0227316 A1 | | 8/2014 | Cohen et al. | |

FOREIGN PATENT DOCUMENTS

| | | | |
|---|---|---|---|
| JP | 2002-531415 | | 9/2002 |
| JP | 2007-512312 | | 5/2007 |
| JP | 2013-514781 | | 5/2013 |
| WO | 2005/049081 | | 6/2005 |
| WO | 2011/075665 | | 6/2011 |
| WO | 2013/042122 | | 3/2013 |
| WO | WO20130420122 | * | 3/2013 |

OTHER PUBLICATIONS

Hamada et al., "Adjuvant Effect of Clarithromycin on Chemotherapy for Murine Lung Cancer", Chemotherapy, vol. 46, No. 1, pp. 49-61, 2000.
Harmon et al., "Influence of Dietary Antibiotics on Antibody Response to Specific Antigens", Journal of Animal Science, vol. 37, No. 5, pp. 1155-1158, 1973.
Hinrichs et al., "Immune Enhancement in Mice by ARA-A", The Journal of Immunology, vol. 130, No. 2, pp. 829-833, 1983.
Kumazawa et al., "The History of Antibiotics: The Japanese Story", Journal of Infection and Chemotherapy, vol. 8, No. 2, pp. 125-133, 2002.
Villarino et al., "The Role of the Macrolide Tulathromycin in Veterinary Medicine", The Veterinary Journal, vol. 198, No. 2, pp. 352-357, 2013.
Slavcheva, E., "Tetracycline and Primary Immune Response", Antibiotiki, vol. 21, No. 1, pp. 75-79, 1976.
International Search Report issued in PCT/JP2016/072797, dated Nov. 1, 2016, along with an English-language translation.
International Preliminary Report on Patentability issued in PCT/JP2016/072797, dated Mar. 17, 2015, along with an English-language translation.
Klinman, Dennis M. et al., "A Single-Dose Combination Therapy That Both Prevents and Treats Anthrax Infection", Vaccine, vol. 27, No. 12, pp. 1811-1815, published online Jan. 31, 2009.
Extended European Search Resport issued in EP Patent Application No. 16833072.8, dated Mar. 11, 2019.
Office Action issued in CN Patent Application No. 201680045906.2 dated Mar. 18, 2020, along with an English language translation.

* cited by examiner

Primary Examiner — Rodney P Swartz
(74) Attorney, Agent, or Firm — Greenblum & Bernstein, P.L.C.

(57) ABSTRACT

The present invention provides an immunity induction-promoting composition which has a track record of use as a medicine or medicinal additive and is capable of safely and effectively inducing cellular immune response, and a vaccine pharmaceutical composition containing the immunity induction-promoting composition. The present invention relates to an immunity induction-promoting composition containing an immunity induction promoter whose active ingredient is an antimicrobial drug.

4 Claims, 1 Drawing Sheet
Specification includes a Sequence Listing.

IMMUNITY INDUCTION PROMOTING COMPOSITION, AND VACCINE PHARMACEUTICAL COMPOSITION

TECHNICAL FIELD

The present invention relates to an immunity induction-promoting composition and a vaccine pharmaceutical composition containing the immunity induction-promoting composition. In particular, the present invention relates to an immunity induction-promoting composition that induces cellular immunity and a vaccine pharmaceutical composition containing the immunity induction-promoting composition. The present invention also relates to a preparation for transdermal administration and a patch preparation each containing the vaccine pharmaceutical composition.

BACKGROUND ART

Vaccines that are generally widely used aim to induce immunity, and are used for administration of pathogens (e.g., microorganisms and viruses) or a part thereof. Also, there are cancer vaccines for inducing specific attack of the immune system to cancer cells by allowing a cellular immune mechanism to recognize a cancer cell-specific antigen. These cancer vaccines are used as one of the means of treating cancer.

Typically, vaccines have to be invasively administered into the body because microorganisms and viruses cannot enter the body through the skin due to their size. Vaccines are thus usually administered by injection. Subcutaneous or intradermal administration by injection, however, have problems such as pain, fear, injection scars and scarring thereof. Injections also have the problems that only medical practitioners are permitted to give them, that intradermal injection, which gives high immune effects, requires proficient skills to give, that the medical practitioners are exposed to the risk of infection due to needle pricking, that the patients have the burden of visiting the hospital in their daily life when repeated administration is required, and that the medical waste which require special disposition, such as injection needles, are generated. Injection is therefore not necessarily the best administration route.

The most common vaccine administration route is subcutaneous or intradermal administration by injection. Yet, various other administration routes have been attempted for immunity induction, such as transdermal administration (Patent Literature 1), buccal, transnasal, and sublingual administrations (Patent Literatures 2 and 3).

Adjuvants practically and commonly used in vaccine administration by injection include aluminum salts (e.g., aluminum hydroxide, aluminum phosphate, and aluminum chloride) and emulsions containing squalene (e.g., MF59 and AS03). Other adjuvants, such as flagellar components, nucleic acids, cytokines, cationic polymers, and polypeptides are also being widely considered. The routes of vaccine administration other than subcutaneous or intradermal administration by injection include transdermal administration and transmucosal administration. As adjuvants for such administration routes, aluminum salts (e.g., aluminum hydroxide, aluminum phosphate, and aluminum chloride) and toxins (e.g., cholera toxin and *Escherichia coli* heat-labile toxin) are being considered, but they are not yet in practical use. Most of them are used as an adjuvant for inducing humoral immunity that produces antibodies for prevention of infectious diseases caused by viruses and bacteria. In contrast, for cellular immunity induction, although Freund's adjuvants, Montanide, GM-CSF, IL-2, IL-12, and IFN-γ are being considered for use in injection, they are not yet in practical use. Also in transdermal administration and mucosal administration, adjuvants for cellular immunity induction have been rarely reported, with only a few reports on toxins such as cholera toxin or *Escherichia coli* heat-labile enterotoxin and nucleic acids.

A large-scale epidemiological investigation reported that patients taking anti-inflammatory agents such as loxoprofen or aspirin have a lower incidence of cancer, but the mechanism is still unclear. One probable reason for the lower incidence is that such anti-inflammatory agents inhibit the production of PGE2 released by cancer cells in metastasis.

To date, limited types of cellular immunity induction promoters have been used, such as Th1 adjuvants (e.g., toll-like receptor ligands that promote differentiation into Th1 cells), Th1 cytokines (e.g., IL-12), and Freund's adjuvants which are oil-based adjuvants that utilize extended release of antigens to enhance the effect. They are insufficient in the balance of safety and effect. In addition, these substances have little or no track record of use as a medicine or medicinal additive. The use of such substances makes it hard to predict the safety and stability of vaccines, providing a major hurdle for vaccine development.

CITATION LIST

Patent Literature

Patent Literature 1: US 2008/0193487
Patent Literature 2: JP 2002-531415 T
Patent Literature 3: US 2008/0112974

SUMMARY OF INVENTION

Technical Problem

In view of the situation in the art, the present invention aims to provide an immunity induction-promoting composition which has a track record of use as a medicine or medicinal additive and is capable of safely and effectively inducing cellular immune response, and a vaccine pharmaceutical composition containing the immunity induction-promoting composition.

Solution to Problem

The present inventors made intensive studies to solve the above problems, and found out that use of an antimicrobial drug, which is one of the medicines, as an active ingredient of an immunity induction promoter enables preparation of an immunity induction-promoting composition capable of safely and effectively inducing cellular immune response. The inventors thus completed the present invention.

The antimicrobial drug in the present invention is also suitable for use in vaccine pharmaceutical compositions, as the drug has a track record of use as a medicine or medicinal additive.

The present invention includes an immunity induction-promoting composition including an immunity induction promoter whose active ingredient is an antimicrobial drug.

Preferably, the antimicrobial drug is at least one selected from the group consisting of a compound that inhibits bacterial cell wall synthesis, a compound that inhibits bacterial protein synthesis, a compound that inhibits bacterial nucleic acid synthesis, a compound that has antifungal activity, and a compound that has antiviral activity.

Preferably, the compound that inhibits bacterial cell wall synthesis has a β-lactam skeleton and/or a fosfomycin skeleton, the compound that inhibits bacterial protein synthesis has at least one selected from the group consisting of an aminoglycoside skeleton, a tetracycline skeleton, a macrolide skeleton, and an amphenicol skeleton, the compound that inhibits bacterial nucleic acid synthesis has a quinolone skeleton, the compound that has antifungal activity has a griseofulvin skeleton and/or an azole skeleton, and the compound that has antiviral activity has a purine skeleton and/or an adamantane skeleton.

Preferably, the compound having a β-lactam skeleton is cefuroxime, the compound having a fosfomycin skeleton is fosfomycin, the compound having an aminoglycoside skeleton is fradiomycin and/or gentamicin, the compound having a tetracycline skeleton is tetracycline and/or minocycline, the compound having a macrolide skeleton is clarithromycin, the compound having an amphenicol skeleton is chloramphenicol, the compound having a quinolone skeleton is norfloxacin, the compound having a griseofulvin skeleton is griseofulvin, the compound having an azole skeleton is miconazole, the compound having a purine skeleton is vidarabine, and the compound having an adamantane skeleton is amantadine.

The present invention also includes a vaccine pharmaceutical composition for immunity induction including: an antigen; and the immunity induction-promoting composition of the present invention.

Preferably, the vaccine pharmaceutical composition of the present invention is administered to a body surface.

Preferably, the vaccine pharmaceutical composition of the present invention is administered by intradermal injection, subcutaneous injection, or intramuscular injection.

Preferably, the vaccine pharmaceutical composition of the present invention is used for inducing cellular immunity.

The present invention will be described below in detail.

The present invention includes an immunity induction-promoting composition containing an immunity induction promoter whose active ingredient is an antimicrobial drug.

Examples of the antimicrobial drug include compounds that inhibit bacterial cell wall synthesis, compounds that inhibit bacterial protein synthesis, compounds that inhibit bacterial nucleic acid synthesis, compounds that have antifungal activity, and compounds that have antiviral activity. In particular, compounds that inhibit bacterial cell wall synthesis, compounds that inhibit bacterial protein synthesis, and/or compounds that inhibit bacterial nucleic acid synthesis are preferred because there is plenty of clinical data of these compounds owing to their long history of development as a medicine and their wide range of indications. Compounds that inhibit bacterial cell wall synthesis and/or compounds that inhibit bacterial protein synthesis are more preferred, with compounds that inhibit bacterial protein synthesis being most preferred.

The compounds that inhibit bacterial cell wall synthesis are not particularly limited. Examples thereof include compounds having a β-lactam skeleton, compounds having a fosfomycin skeleton, compounds having an isonicotinic acid skeleton, and compounds having a glycopeptide skeleton. In particular, compounds having a β-lactam skeleton and/or compounds having a fosfomycin skeleton are preferred.

The compounds that inhibit bacterial protein synthesis are not particularly limited. Examples thereof include compounds having an aminoglycoside skeleton, compounds having a tetracycline skeleton, compounds having a macrolide skeleton, and compounds having an amphenicol skeleton. In particular, compounds having an aminoglycoside skeleton and compounds having a tetracycline skeleton, which act on a 30S ribosomal subunit, are preferred.

The compounds that inhibit bacterial nucleic acid synthesis are not particularly limited. Examples thereof include compounds having a quinolone skeleton and compounds having an aminosalicylic acid skeleton. In particular, compounds having a quinolone skeleton are preferred.

The compounds that have antifungal activity are not particularly limited. Examples thereof include compounds having a griseofulvin skeleton, compounds having an azole skeleton, and compounds having a benzylamine skeleton. In particular, compounds having a griseofulvin skeleton and/or compounds having an azole skeleton are preferred, with compounds having a griseofulvin skeleton being more preferred.

The compounds that have antiviral activity are not particularly limited. Examples thereof include compounds having a purine skeleton and/or compounds having an adamantane skeleton. In particular, compounds having a purine skeleton are preferred.

Preferred compounds usable as the antimicrobial drug are compounds having an aminoglycoside skeleton, compounds having a tetracycline skeleton, compounds having a β-lactam skeleton, compounds having a griseofulvin skeleton, compounds having a quinolone skeleton, compounds having a purine skeleton, compounds having a fosfomycin skeleton, compounds having an adamantane skeleton, compounds having an azole skeleton, compounds having a macrolide skeleton, and compounds having an amphenicol skeleton. More preferred are compounds having an aminoglycoside skeleton, compounds having a tetracycline skeleton, compounds having a R-lactam skeleton, compounds having a griseofulvin skeleton, compounds having a quinolone skeleton, compounds having a purine skeleton, and compounds having a fosfomycin skeleton. Most preferred are compounds having an aminoglycoside skeleton and compounds having a tetracycline skeleton.

The compounds having a β-lactam skeleton are not particularly limited. Suitable compounds having a @-lactam skeleton include penicillin G, ampicillin, cloxacillin, bacampicillin, cefazolin, cefaclor, cephalexin, cefotiam, cefuroxime, cefotaxime, cefixime, cefdinir, cefoselis, cefmetazole, cefminox, latamoxef, panipenem, meropenem, faropenem, aztreonam, carumonam, and pharmaceutically acceptable salts thereof. These compounds having a β-lactam skeleton may be used alone or in combination of two or more thereof. In particular, cefuroxime is preferred because it is stable against β-lactamase.

The compounds having a fosfomycin skeleton are not particularly limited. Examples thereof include fosfomycin. These compounds having a fosfomycin skeleton may be used alone or in combination of two or more thereof.

The compounds having an isonicotinic acid skeleton are not particularly limited. Examples thereof include isoniazid. These compounds having an isonicotinic acid skeleton may be used alone or in combination of two or more thereof.

The compounds having a glycopeptide skeleton are not particularly limited. Examples thereof include vancomycin and teicoplanin. In particular, vancomycin is preferred. These compounds having a glycopeptide skeleton may be used alone or in combination of two or more thereof.

The compounds having an aminoglycoside skeleton are not particularly limited. Examples thereof include streptomycin, fradiomycin, kanamycin, gentamicin, tobramycin, amikacin, dibekacin, and arbekacin. In particular, fradiomycin and/or gentamicin are/is preferred. These compounds having an aminoglycoside skeleton may be used alone or in combination of two or more thereof.

The compounds having a tetracycline skeleton are not particularly limited. Examples thereof include tetracycline, chlortetracycline, minocycline, doxycycline, oxytetracycline, and demeclocycline. In particular, tetracycline and/or minocycline are/is preferred. These compounds having a tetracycline skeleton may be used alone or in combination of two or more thereof.

The compounds having a macrolide skeleton are not particularly limited. Examples thereof include clarithromycin, josamycin, rokitamycin, erythromycin, azithromycin, oleandomycin, kitasamycin, josamycin, acetylspiramycin, and midecamycin. In particular, clarithromycin is preferred. These compounds having a macrolide skeleton may be used alone or in combination of two or more thereof.

The compounds having an amphenicol skeleton are not particularly limited. Examples thereof include chloramphenicol and thiamphenicol. In particular, chloramphenicol is preferred. These compounds having an amphenicol skeleton may be used alone or in combination of two or more thereof.

The compounds having a quinolone skeleton are not particularly limited. Examples thereof include nalidixic acid, piromidic acid, pipemidic acid, norfloxacin, ofloxacin, enoxacin, ciprofloxacin, lomefloxacin, levofloxacin, garenoxacin, fleroxacin, sitafloxacin, tosufloxacin, sparfloxacin, gatifloxacin, and moxifloxacin. In particular, norfloxacin is preferred. These compounds having a quinolone skeleton may be used alone or in combination of two or more thereof.

The compounds having an aminosalicylic acid skeleton are not particularly limited. Examples thereof include sulfamethoxazole and para-aminosalicylate. In particular, sulfamethoxazole is preferred. These compounds having an aminosalicylic acid skeleton may be used alone or in combination of two or more thereof.

The compounds having a griseofulvin skeleton are not particularly limited. Examples thereof include griseofulvin. These compounds having a griseofulvin skeleton may be used alone or in combination of two or more thereof.

The compounds having an azole skeleton are not particularly limited. Examples thereof include miconazole, fluconazole, and itraconazole. In particular, miconazole is preferred. These compounds having an azole skeleton may be used alone or in combination of two or more thereof.

The compounds having a benzylamine skeleton are not particularly limited. Examples thereof include butenafine. These compounds having a benzylamine skeleton may be used alone or in combination of two or more thereof.

The compounds having a purine skeleton are not particularly limited. Examples thereof include vidarabine, aciclovir, and ganciclovir. In particular, vidarabine is preferred. These compounds having a purine skeleton may be used alone or in combination of two or more thereof.

The compounds having an adamantane skeleton are not particularly limited. Examples thereof include amantadine. These compounds having an adamantane skeleton may be used alone or in combination of two or more thereof.

The present invention also includes a vaccine pharmaceutical composition for immunity induction including an antigen and the immunity induction-promoting composition of the present invention.

The antigen may be any substance capable of inducing an immune response. Any antigen may be used. Examples thereof include proteins and peptides. For transdermal administration which requires skin penetration of the antigen, antigens having small molecular weights are preferred. For example, a peptide having about 8 to 12 amino acid residues may be used.

The antigen is not particularly limited, and examples thereof include a cancer antigen peptide and an antigen derived from an infectious pathogen.

As used herein, the term "cancer" refers to the abnormal expression of oncogene. Examples of the cancer include a cancer associated with overexpression, such as a hematopoietic tumor or solid cancer.

As used herein, the term "abnormal expression of a gene" means that the expression level of a gene in a cell is significantly increased or decreased by, for example, at least two times or at least four times, as compared to another cell in the same tissue.

As used herein, the term "overexpression" means an abnormal increase in the expression level. The expression level of a gene can be easily measured by any method known in the relevant technical field.

Examples of the oncogene include survivin gene, GPC3 gene, HER2/neu gene, MAGE-3 gene, MAGE-A1 gene, MAGE-A3/A6 gene, MAGE-A4 gene, MAGE-12 gene, proteinase-3 gene, AFP gene, CA-125 gene, CD44 gene, CEA gene, c-Kit gene, c-met gene, c-myc gene, L-myc gene, COX2 gene, CyclinD1 gene, Cytokeratin-7 gene, Cytokeratin-19 gene, Cytokeratin-20 gene, E2F1 gene, E2F3 gene, EGFR gene, Gli1 gene, hCGβ gene, HIF-1α gene, HnRNP A2/B1 gene, hTERT gene, MDM gene, MDR-1 gene, MMP-2 gene, MMP-9 gene, Muc-1 gene, Muc-4 gene, Muc-7 gene, NSE gene, ProGRP gene, PSA gene, RCAS1 gene, SCC gene, thymoglobulin gene, VEGF-A gene, and VEGF-A gene.

Non-limiting examples of cancers associated with abnormal expression of the survivin gene include malignant lymphoma, bladder cancer, lung cancer, and large bowel cancer. Non-liming examples of cancers associated with abnormal expression of the GPC3 gene include liver cancer, bile duct cancer, and stomach cancer. Non-liming examples of cancers associated with abnormal expression of the HER2/neu gene include breast cancer, stomach cancer, ovarian cancer, uterine cancer, bladder cancer, non-small cell lung cancer, and prostatic cancer. Non-liming examples of cancers associated with abnormal expression of the MAGE-3 gene include melanoma, lung cancer, head and neck cancer, bladder cancer, stomach cancer, esophageal cancer, and liver cancer. Non-liming examples of cancers associated with abnormal expression of the proteinase-3 gene include acute myelocytic leukemia and pancreatic cancer.

As used herein, the term "cancer antigen" refers to a substance such as a protein or peptide which is specifically expressed in tumor cells or cancer cells and capable of inducing cellular immune response.

As used herein, the term "cancer antigen peptide" refers to a partial peptide derived from a cancer antigen protein, capable of inducing cellular immune response. Usually, a cancer antigen peptide is produced by decomposition of a cancer antigen protein (which is an oncogene product) in a cancer cell, and is presented on the surface of a cancer cell by MHC class I molecules.

The cancer antigen peptide may be an endogenous cancer antigen peptide isolated and purified from cancer cells, or may be a synthetic peptide having the same amino acid sequence as the endogenous cancer antigen peptide. Specifically, preferred examples of the cancer antigen peptide include survivin 2B peptide, GPC3 peptide, HER2/neu_A24 peptide, MAGE3_A24 peptide, PR1 peptide, HER2/ neu_A02 peptide, MAGE3_A02 peptide, HER2/neu_E75 peptide, MUC1 peptide, and altered peptides thereof.

As used herein, the term "survivin 2B peptide" refers to a peptide derived from survivin which is an oncogene product, having the sequence Ala Tyr Ala Cys Asn Thr Ser Thr Leu (SEQ ID No: 1).

As used herein, the term "GPC3 peptide" refers to a peptide derived from GPC3 which is an oncogene product, having the sequence Glu Tyr Ile Leu Ser Leu Glu Glu Leu (SEQ ID No: 2).

As used herein, the term "HER2/neu_A24 peptide" refers to an HLA-A24-restricted peptide derived from HER2/neu which is an oncogene product, having the sequence Thr Tyr Leu Pro Thr Asn Ala Ser Leu (SEQ ID No: 3).

As used herein, the term "MAGE3_A24 peptide" refers to an HLA-A24-restricted peptide derived from MAGE-3 which is an oncogene product, having the sequence Ile Met Pro Lys Ala Gly Leu Leu Ile (SEQ ID No: 4).

As used herein, the term "PR1 peptide" refers to a peptide derived from proteinase-3 which is an oncogene product, having the sequence Val Leu Gln Glu Leu Asn Val Thr Val (SEQ ID No: 5).

As used herein, the term "HER2/neu_A02 peptide" refers to an HLA-A02-restricted peptide derived from HER2/neu which is an oncogene product, having the sequence Lys Val Phe Gly Ser Leu Ala Phe Val (SEQ ID No: 6).

As used herein, the term "MAGE3_A02 peptide" refers to an HLA-A02-restricted peptide derived from MAGE-3 which is an oncogene product, having the sequence Lys Val Ala Glu Ile Val His Phe Leu (SEQ ID No: 7).

As used herein, the term "HER2/neu_E75 peptide" refers to a peptide derived from a product (HER2 protein) of an oncogene HER2/neu, having the sequence Lys Ile Phe Gly Ser Leu Ala Phe Leu (SEQ ID No: 8).

As used herein, the term "MUC1 peptide" refers to a peptide derived from MUC1 protein which is a glycoprotein that is highly expressed on many cancer cells, having the sequence Ser Thr Ala Pro Pro Val His Asn Val (SEQ ID No: 9).

As used herein, the term "altered peptide" refers to a peptide in which all or a part of amino acids are altered by, for example, substitution or modification.

The altered peptide is not particularly limited, and examples thereof include peptides such as: (a) a peptide having an amino acid sequence in which one to several amino acids (for example, 1, 2, 3, 4, or 5 amino acids) are substituted, deleted, or added in the amino acid sequence of the peptide; and (b) a peptide having an amino acid sequence in which all or a part of amino acids (for example, 1, 2, 3, 4, 5, 6, 7, 8, 9, or 10 amino acids) are modified in the amino acid sequence of the peptide.

The amino acids of the altered peptide may be modified in any manner. Examples of such modifications include acetylation; alkylation such as methylation; glycosylation; hydroxylation; carboxylation; aldehydation; phosphorylation; sulfonylation; formylation; aliphatic chain addition modification such as myristoylation, palmitoylation, and stearoylation; octanoylation; esterification; amidation; deamidation; disulfide bond formation modification such as cystine modification, glutathione modification, and thioglycolic acid modification; glycation; ubiquitination; succinimide formation; glutamylation; and prenylation.

The altered peptide may contain substitution, deletion, or addition of one or more amino acids and modification of one or more amino acids in combination.

As used herein, the term "infectious pathogen-derived antigen" refers to an infectious pathogen or its component or a substance derived from an infectious pathogen or its component, capable of inducing cellular immune response. Thus, it is possible to treat or prevent an infectious disease by administering the infectious pathogen-derived antigen together with the immunity induction promoter whose active ingredient is an antimicrobial drug to a subject.

The infectious pathogen-derived antigen is preferably IPEP87 peptide, HBVenv peptide, or an altered peptide of IPEP87 peptide or HBVenv peptide.

As used herein, the term "IPEP87 peptide" refers to a peptide derived from a hepatitis C virus (HCV) protein, having the sequence Asp Leu Met Gly Tyr Ile Pro Ala Val (SEQ ID No: 10).

As used herein, the term "HBVenv peptide" refers to a peptide derived from a hepatitis B virus (HBV) protein, having the sequence Trp Leu Ser Leu Leu Val Pro Phe Val (SEQ ID No: 11).

As used herein, the term "infectious disease" refers to a disease caused by infection with an infectious pathogen, growth of an infectious pathogen, or the like.

The infectious disease is not particularly limited. Examples thereof include hepatitis A, hepatitis B, hepatitis C, hepatitis D, hepatitis E, cervical cancer, condyloma acuminata, HIV infectious diseases, genital chlamydia, and herpes simplex.

The peptides mentioned above can be in the free form or any pharmacologically acceptable salt form.

Examples of the pharmacologically acceptable salt form include acid salts (e.g., acetate, TFA salt, hydrochloride, sulfate, phosphate, lactate, tartrate, maleate, fumarate, oxalate, hydrobromate, succinate, nitrate, malate, citrate, oleate, palmitate, propionate, formate, benzoate, picrate, benzenesulfonate, dodecylsulfate, methanesulfonate, p-toluenesulfonate, glutarate, and various amino acid salts), metal salts (e.g., alkali metal salts (e.g., sodium salt and potassium salt), alkaline-earth metal salts (e.g., calcium salt and magnesium salt), and aluminum salt), and amine salts (e.g., triethylamine salt, benzylamine salt, diethanolamine salt, t-butylamine salt, dicyclohexylamine salt, arginine salt, dimethylammonium salt, and ammonium salt). In particular, acetate or TFA salt is preferred.

The peptides mentioned above can be synthesized or produced, isolated, and purified by a well-known method.

In the vaccine pharmaceutical composition of the present invention, the amount of the immunity induction-promoting composition containing the immunity induction promoter whose active ingredient is an antimicrobial drug is not particularly limited. The lower limit of the amount is preferably 0.001 parts by weight relative to 1 part by weight of the antigen, and the upper limit is preferably 1000 parts by weight. If the amount is less than 0.001 parts by weight, the immunity-inducing effect may be insufficient. If the amount is more than 1000 parts by weight, safety issues may arise. The lower limit of the amount is more preferably 0.005 parts by weight, and the upper limit is more preferably 500 parts by weight. The lower limit is still more preferably 0.01 parts by weight, and the upper limit is still more preferably 100 parts by weight.

The vaccine pharmaceutical composition of the present invention preferably further contains a second immunity induction promoter that is a helper peptide, in addition to the immunity induction promoter whose active ingredient is an antimicrobial drug (hereinafter also referred to as a first immunity induction promoter).

The additional use of the second immunity induction promoter that is a helper peptide can further promote cellular immunity.

As used herein, the term "helper peptide" refers to any peptide that activates helper-T cells.

Examples of the second immunity induction promoter that is a helper peptide include a helper peptide derived from tubercle bacillus, a helper peptide derived from measles virus, a helper peptide derived from hepatitis B virus, a helper peptide derived from hepatitis C virus, a helper peptide derived from *Chlamydia trachomatis*, a helper peptide derived from *P. falciparum* sporozoite, a helper peptide derived from keyhole limpet haemocyanin, a helper peptide derived from tetanus toxin, a helper peptide derived from pertussis toxin, a helper peptide derived from diphtheria toxin, helper peptides derived from cancer cells (e.g., IMA-MMP-001 helper peptide, CEA-006 helper peptide, MMP-001 helper peptide, TGFBI-004 helper peptide, HER-2/neu (aa776-790) helper peptide, AE36 helper peptide, AE37 helper peptide, MET-005 helper peptide, and BIR-002 helper peptide), and universal helper analogs (e.g., PADRE), and altered peptides thereof. Preferred among these are Peptide-25, altered Peptide-25, and PADRE. Examples of the altered Peptide-25 include Peptide-25B.

As used herein, the term "Peptide-25" refers to a 15-amino acid peptide corresponding to amino acid residues 240 to 254 of Ag85B that is a key protein secreted by human tubercle bacillus (*Mycobacterium tuberculosis*) and having the sequence Phe Gln Asp Ala Tyr Asn Ala Ala Gly Gly His Asn Ala Val Phe (SEQ ID No: 12).

As used herein, the term "Peptide-25B" refers to a 15-amino acid peptide prepared by partially altering amino acids of Peptide-25 with an aim of enhancing the immunostimulation effect and having the sequence Phe Gln Asp Ala Tyr Asn Ala Val His Ala Ala His Ala Val Phe (SEQ ID No: 13).

As used herein, the term "PADRE" refers to a 13-amino acid peptide having the sequence D-Ala Lys cyclohexyl-Ala Val Ala Ala Trp Thr Leu Lys Ala Ala D-Ala (SEQ ID No: 14).

The amount of the second immunity induction promoter that is a helper peptide in the vaccine pharmaceutical composition of the present invention is not particularly limited. The lower limit is preferably 0.01 parts by weight and the upper limit is preferably 100 parts by weight relative to 1 part by weight of the antigen. If the amount is less than 0.01 parts by weight, cellular immunity may not be sufficiently promoted. If the amount is more than 100 parts by weight, safety issues may arise. The lower limit of the amount is more preferably 0.1 parts by weight and the upper limit thereof is more preferably 10 parts by weight.

The present invention also includes a vaccine pharmaceutical composition which contains the antigen and the immunity induction-promoting composition of the present invention and which is administered to a body surface to strongly induce cellular immunity against the antigen. Simultaneous administration of the antigen with the antimicrobial drug to a body surface (transdermal administration or mucosal administration) can more strongly induce cellular immunity than administration of the antigen alone. In other words, the vaccine pharmaceutical composition of the present invention may be a vaccine pharmaceutical composition for intradermal, subcutaneous, or intramuscular administration, but is preferably a vaccine pharmaceutical composition for transdermal administration or transmucosal administration. Transdermal administration or transmucosal administration of the vaccine pharmaceutical composition of the present invention to the subject can effectively induce an antigen-specific cellular immunity.

As used herein, the term "subject" refers to any animal in which administration of the vaccine pharmaceutical composition in practical use may induce an immune response. Typically, the term refers to mammals including human, mouse, rat, canine, feline, leporine, equine, bovine, ovine, porcine, caprine, simian, and chimpanzee. A particularly preferred subject is a human.

<Vaccine Pharmaceutical Composition for Transdermal Administration>

The dosage form of the vaccine pharmaceutical composition for transdermal administration may be any preparation usually used for transdermal administration. For example, the vaccine pharmaceutical composition of the present invention may be a solution for external application such as a liniment or a lotion; a spray for external application such as an aerosol; a gel; a patch such as a tape, or a poultice; an ointment, a plaster, or a cream. Categories, definitions, properties, production processes, and the like of these formulations are well known in the relevant art. For example, see the Japanese Pharmacopoeia, 16th Edition. Any known material may be used for these formulations.

Among the above dosage forms, preferred are a cream, an ointment, and a patch (tape, poultice).

The present invention also includes a preparation for transdermal administration containing the transdermal vaccine pharmaceutical composition of the present invention.

In the vaccine pharmaceutical composition for transdermal administration (in the case of a tape, in the adhesive layer), the amounts of the antigen and the immunity induction-promoting composition containing the immunity induction promoter whose active ingredient is an antimicrobial drug are not particularly limited. The amount of the antigen is preferably 0.01 to 40% by weight, more preferably 0.1 to 30% by weight. The amount of the immunity induction-promoting composition is preferably 0.001 to 30% by weight, more preferably 0.01 to 20% by weight.

Examples of a base usable for the liniment include water, ethanol, fatty oils, hard paraffin, soft paraffin, liquid paraffin, glycerin, paraffin oil, beeswax, metal soap, mucilage, natural oils (such as almond oil, corn oil, peanut oil, castor oil, olive oil, and derivatives thereof (e.g., polyoxyl castor oil)), mutton tallow or derivatives thereof, and fatty acids and/or esters (e.g., stearic acid, oleic acid, and isopropyl myristate).

The lotion is a formulation containing ingredients (i.e., the antigen, the immunity induction promoter whose active ingredient is an antimicrobial drug) finely and homogeneously dispersed in an aqueous solution, and may be a suspension-type lotion or an emulsion-type lotion.

Examples of the suspending agent include gum arabic, sodium alginate, sodium carboxymethyl cellulose, methylcellulose, and bentonite. Examples of the emulsifier include sodium lauryl sulfate and sorbitan fatty acid esters.

Examples of a base usable for the ointment include those commonly used as hydrophobic bases such as oils/fats, waxes, or hydrocarbon compounds. Specific examples of the base for the ointment include mineral bases such as yellow Vaseline, white Vaseline, paraffin, liquid paraffin, plastibase, and silicone, and animal or plant bases such as beeswax and animal or plant fats and/or oils.

Examples of a base usable for the cream include water/oil-type bases such as hydrophilic ointment and vanishing cream; and oil/water-type bases such as hydrophilic Vaseline, purified lanolin, Aquaphor, Eucerin, Neocerin, hydrous lanolin, cold cream, and hydrophilic plastibase.

Examples of the base usable for the gel include hydrogel base such as carboxyvinyl polymers, gel bases, fat-free ointment, polyvinylpyrrolidone, polyvinyl alcohol, sodium polyacrylate, carboxymethyl cellulose, starch, xanthan gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, psyllium seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl aminoacetate, casein, alkyl alginate ester, gelatin, and polyethylene glycol.

Examples of the base usable for the poultice include gelatin, sodium carboxymethyl cellulose, methylcellulose, sodium polyacrylate, kaolin, polyvinyl alcohol, polyvinylpyrrolidone, glycerin, propylene glycol, and water.

The tape preferably includes an adhesive layer containing ingredients (i.e., the antigen, the immunity induction promoter whose active ingredient is an antimicrobial drug), and a support that supports the adhesive layer. The tape may further include a release liner that prevents exposure of the adhesive layer before use and that can be easily removed from the adhesive layer at the time of use.

Any adhesive may be used to form the adhesive layer. Examples of adhesives include acrylic adhesives containing acrylic polymers; rubber adhesives containing rubber elastomers such as styrene/diene/styrene block copolymers (e.g., styrene/isoprene/styrene (SIS) block copolymer and styrene/butadiene/styrene block copolymer), polyisoprene, polyisobutylene (PIB), butyl rubber, and polybutadiene; silicone adhesives such as silicone rubber, dimethylsiloxane adhesives, and diphenylsiloxane adhesives; vinyl ether adhesives such as polyvinyl methyl ether, polyvinyl ethyl ether, and polyvinyl isobutyl ether; vinyl ester adhesives such as vinyl acetate-ethylene copolymer; and polyester adhesives containing a carboxylic acid component (e.g., dimethyl terephthalate, dimethyl isophthalate, and dimethyl phthalate) and a polyhydric alcohol component (e.g., ethylene glycol). Particularly preferred adhesives are acrylic adhesives, rubber adhesives, and silicone adhesives.

The amount of the adhesive in the adhesive layer is not particularly limited, and is preferably 10 to 90% by weight, more preferably 20 to 80% by weight in terms of solids relative to the total weight of the adhesive layer.

The acrylic adhesive may be an acrylate adhesive containing, as a main component, a polymer that contains a C2-C18 alkyl (meth)acrylate as a first monomer.

Examples of the alkyl (meth)acrylate (first monomer) include alkyl (meth)acrylates containing a C1-C18 linear, branched, or cyclic alkyl group (e.g., methyl, ethyl, propyl, butyl, pentyl, hexyl, cyclohexyl, heptyl, octyl, 2-ethylhexyl, nonyl, decyl, undecyl, dodecyl, and tridecyl). Preferred among these are alkyl (meth)acrylate containing C4-C18 linear, branched, or cyclic alkyl group. Further, since a monomer component that lowers the glass transition temperature of a polymer is suitably used to impart adhesiveness at room temperature, an alkyl (meth)acrylate having a C4-C8 linear, branched, or cyclic alkyl group (e.g., butyl, pentyl, hexyl, cyclohexyl, heptyl, octyl, 2-ethylhexyl; preferably butyl, 2-ethylhexyl, or cyclohexyl; particularly preferably 2-ethylhexyl) is more preferred.

Specifically, the alkyl (meth)acrylate (first monomer) is preferably butyl acrylate, 2-ethylhexyl acrylate, 2-ethylhexyl methacrylate, cyclohexyl acrylate, or cyclohexyl methacrylate, particularly preferably 2-ethylhexyl acrylate. These alkyl (meth)acrylates (first monomers) may be used alone or in combination of two or more thereof.

The acrylic adhesive may contain a second monomer copolymerizable with the alkyl (meth)acrylate (first monomer). Such a second monomer may be a monomer having a functional group that can form a crosslinking point when a crosslinking agent is used. Examples of functional groups capable of being involved in crosslinking reactions include groups such as hydroxy, carboxy, and vinyl groups. Among these, hydroxy and carboxy groups are preferred.

Specific examples of the second monomer include hydroxyethyl (meth)acrylate, hydroxypropyl (meth)acrylate, N-hydroxyalkyl (meth)acrylamide, (meth)acrylic acid, itaconic acid, maleic acid, maleic anhydride, mesaconic acid, citraconic acid, and glutaconic acid. Among these, acrylic acid, methacrylic acid, hydroxyethyl acrylate (particularly, 2-hydroxyethyl acrylate) are preferred, and acrylic acid is the most preferred, in view of easy availability. These second monomers may be used alone or in combination of two or more thereof.

Moreover, the acrylic adhesive may contain a third monomer in addition to the first monomer and second monomer.

Examples of the third monomer include vinyl esters such as vinyl acetate and vinyl propionate; vinyl ethers such as methyl vinyl ether and ethyl vinyl ether; vinyl amides such as N-vinyl-2-pyrrolidone and N-vinylcaprolactam; alkoxy (meth)acrylates such as methoxyethyl (meth)acrylate, ethoxyethyl (meth)acrylate, and tetrahydrofurfuryl (meth)acrylate; hydroxy group-containing monomers (as the third monomer, not as a crosslinking point) such as hydroxypropyl(meth)acrylate and α-hydroxymethyl acrylate; (meth)acrylic acid derivatives having an amide group such as (meth)acrylamide, dimethyl (meth)acrylamide, N-butyl (meth)acrylamide, and N-methylol (meth)acrylamide; aminoalkyl (meth)acrylates such as aminoethyl (meth)acrylate, dimethylaminoethyl (meth)acrylate, and t-butyl aminoethyl (meth)acrylate; alkoxyalkylene glycol (meth)acrylates such as methoxyethylene glycol (meth)acrylate, methoxydiethylene glycol (meth)acrylate, methoxypolyethylene glycol (meth)acrylate, and methoxypolypropylene glycol (meth) acrylate; (meth)acrylonitrile; monomers containing sulfonic acid such as styrenesulfonic acid, allylsulfonic acid, sulfopropyl(meth)acrylate, (meth)acryloyloxy naphthalene sulfonate, and acrylamide methylsulfonate; and vinyl group-containing monomers such as vinylpiperidone, vinylpyrimidine, vinylpiperazine, vinylpyrrole, vinylimidazole, vinyloxazole, and vinylmorpholine. Preferred among these are vinyl esters and vinyl amides. Vinyl acetate is preferred among vinyl esters, and N-vinyl-2-pyrrolidone is preferred among vinyl amides. These third monomers may be used alone or in combination of two or more thereof.

In the case of a copolymer of the alkyl (meth)acrylate (first monomer) and the vinyl monomer having a functional group capable of being involved in crosslinking reaction (second monomer), the alkyl (meth)acrylate and the vinyl monomer having a functional group capable of being involved in crosslinking reaction are preferably copolymerized at a weight ratio of (99-85):(1-15), more preferably at a weight ratio of (99-90):(1-10).

In the case of a copolymer of the alkyl (meth)acrylate (first monomer), the vinyl monomer having a functional group that can be involved in a crosslinking reaction (second monomer), and a different monomer other than these (third monomer), the alkyl (meth)acrylate, the vinyl monomer having a functional group capable of being involved in crosslinking reaction, and the different monomer are preferably copolymerized at a weight ratio of (40-94):(1-15):(5-50), more preferably at a weight ratio of (50-89):(1-10):(10-40).

The polymerization reaction may be carried out by any conventionally known method. For example, the above monomers may be reacted in the presence of an initiator (e.g., benzoyl peroxide or azobisisobutyronitrile) in a solvent (e.g., ethyl acetate) at 50° C. to 70° C. for 5 to 48 hours.

The acrylic adhesive more preferably contains a 2-ethylhexyl acrylate/acrylic acid/N-vinyl-2-pyrrolidone copolymer, a 2-ethylhexyl acrylate/N-(2-hydroxyethyl)acrylamide/N-vinyl-2-pyrrolidone copolymer, a 2-ethylhexyl acrylate/2-hydroxyethyl acrylate/vinyl acetate copolymer, or a 2-ethylhexyl acrylate/acrylic acid copolymer, particularly preferably contains a 2-ethylhexyl acrylate/acrylic acid/N-vinyl-2-pyrrolidone copolymer.

The acrylic adhesive may be subjected to physical crosslinking treatment by radiation such as ultraviolet irradiation or electron beam irradiation, or chemical crosslinking treatment using various crosslinking agents such as an isocyanate compound (e.g., trifunctional isocyanate), an organic peroxide, an organic metal salt, a metal alcoholate, a metal chelate compound, or a polyfunctional compound (e.g., a polyfunctional external crosslinking agent, a polyfunctional monomer for internal crosslinking such as di(meth)acrylate).

The acrylic adhesive is preferably impermeable to the cellular immunity induction promoter. In other words, it is preferably one that prevents a decrease in the amounts of the peptide contained in the adhesive layer, the cellular immunity induction promoter, and additives by not allowing them to pass through the support and escape from the back side.

Any rubber elastomer may be used for preparing the rubber adhesive, and examples thereof include polyisobutylene/polybutene elastomer, a styrene/diene/styrene block copolymer, styrene/butadiene elastomer, nitrile elastomer, chloroprene elastomer, vinylpyridine elastomer, polyisobutylene elastomer, butyl elastomer, and isoprene-isobutylene elastomer. Preferred among these are polyisobutylene (PIB) and a styrene/diene/styrene block copolymer (such as a styrene/butadiene/styrene block copolymer (SBS) or a styrene/isoprene/styrene block copolymer (SIS)), in view of solubility to the ingredients and the skin adhesiveness. These rubber elastomers may be used alone or in combination of two or more thereof.

In order to achieve appropriate adhesion and solubility to the ingredients, the rubber adhesive may be a mixture of rubber elastomers formed from the same or different components and different in the average molecular weight. For example, a mixture of a high-molecular-weight polyisobutylene having an average molecular weight of 150,000 to 5,500,000 and a medium-molecular-weight polyisobutylene having an average molecular weight of 10,000 to 150,000 and/or a low-molecular-weight polyisobutylene having an average molecular weight of 500 to 4,000 is preferred. The amount of the high-molecular-weight polyisobutylene is 10 to 80% by weight, preferably 20 to 70% by weight, relative to the total amount of the polyisobutylenes. The amount of the medium-molecular-weight polyisobutylene is 0 to 90% by weight, preferably 10 to 80% by weight, relative to the total amount of the polyisobutylenes. The amount of the low-molecular-weight polyisobutylene is 0 to 80% by weight, preferably 10 to 60% by weight, relative to the total amount of the polyisobutylenes.

As user herein, the term "average molecular weight" refers to a viscosity average molecular weight calculated from the Flory viscosity equation. The average molecular weight is determined by calculating the Staudinger index ($J_0$) from the flow time at 20° C. of the capillary 1 of an Ubbelohde viscometer by the Schulz-Blaschke equation, and using this $J_0$ value in the following expression.

$$J_0 = n_{sp}/c(1+0.3\ n_{sp})$$ (Schulz-Blaschke equation)

$$n_{sp} = t/t_0 - 1$$

t: Flow time of solution (according to Hagenbach-couette correction formula)
$t_0$: Flow time of solvent (according to Hagenbach-couette correction formula)
c: Concentration of solution (g/cm$^3$)

$$J_0 = 3.06 \times 10^{-2} \overline{M_v}^{0.66}$$

$\overline{M_v}$: Viscosity average molecular weight

In order to provide appropriate tackiness, the rubber adhesive may contain a tackifier such as rosin resin, polyterpene resin, coumarone-indene resin, petroleum resin, terpene-phenol resin, xylene resin, or alicyclic saturated hydrocarbon resin. These tackifiers may be used alone or in combination of two or more thereof.

The amount of the tackifier is preferably 50% by weight or less, more preferably 5 to 40% by weight relative to the total weight of the rubber adhesive.

Examples of the silicone adhesive include polyorganosiloxane adhesives, polydimethylsiloxane adhesives, and polydimethyldiphenyl-siloxane adhesives. In particular, commercially available silicone adhesives such as BIO PSA (Dow Corning Corporation) are preferred.

The adhesive layer may further contain a skin permeation enhancer.

As used herein, the term "skin permeation enhancer" means any substance that may improve the efficiency of skin permeation of a transdermally administered antigen as compared with the efficiency obtained without the substance.

The skin permeation enhancer is preferably liquid (i.e., having fluidity) at room temperature (25° C.). In the case where two or more kinds of skin permeation enhancers are mixed, the final mixture is preferably liquid at room temperature (25° C.) and has an effect of enhancing skin permeation. Such an organic liquid component is preferably a hydrophobic liquid component in terms of the compatibility in the adhesive.

Examples of the skin permeation enhancer include higher alcohols, fatty acid esters, and polyhydric alcohol fatty acid esters. The higher alcohol is preferably a C8-C18 higher alcohol, more preferably a C8-C14 higher alcohol. The fatty acid ester is preferably a fatty acid ester of a C8-C18 fatty acid and a C1-C18 monohydric alcohol, more preferably a fatty acid ester of a C12-C16 fatty acid and a C1-C18 monohydric alcohol. In particular, preferred are fatty acid esters, and particularly preferred are isopropyl myristate, isopropyl palmitate, and diethyl sebacate.

Specific examples of the skin permeation enhancer include higher alcohols such as oleyl alcohol and octyl dodecanol; polyhydric alcohols such as glycerin, ethylene glycol, and polypropylene glycol; higher fatty acids such as oleic acid and caprylic acid; fatty acid esters such as isopropyl myristate, isopropyl palmitate, and ethyl oleate; polybasic acid esters such as diethyl sebacate and diisopropyl adipate; polyhydric alcohol fatty acid esters such as diglyceryl triisostearate, sorbitan monooleate, propylene glycol dicaprylate, polyethylene glycol monolaurate, and polyoxyethylene sorbitol tetraoleate; polyoxyethylene alkyl ethers such as polyoxyethylene lauryl ether; hydrocarbons such as squalane or liquid paraffin; vegetable oils such as olive oil and castor oil; silicone oil; pyrrolidones such as N-methylpyrrolidone and N-dodecyl pyrrolidone; and sulfoxides such as decyl methyl sulfoxide. These skin permeation enhancers may be used alone or in combination of two or more thereof.

In the case of using the acrylic adhesive or rubber adhesive, the skin permeation enhancer used may be, for example, polyvinyl pyrrolidone, crospovidone, polypropylene glycol, polyvinyl alcohol, carboxy vinyl polymer, hydroxypropyl cellulose, or a mixture of these. Preferred among these are polyvinyl pyrrolidone, crospovidone, and polypropylene glycol.

The amount of the skin permeation enhancer in the vaccine pharmaceutical composition is not particularly limited, and is preferably 0.1 to 70% by weight, more preferably 1 to 65% by weight, still more preferably 5 to 60% by weight, relative to the total weight of the vaccine pharmaceutical composition (in the case of a tape, the adhesive layer). When the amount of the skin permeation enhancer is 0.1% by weight or more, the effect of promoting skin permeation is high. When the amount of the skin permeation enhancer is 70% by weight or less, the effect of promoting skin permeation is high, while reduction in the adhesion and the cohesion of the entire vaccine pharmaceutical composition (in the case of a tape, the adhesive layer) is suppressed.

The adhesive layer may have any thickness. Preferably, the thickness is 10 to 1,000 μm. With the thickness within the above range, the adhesive layer can readily contain the ingredients each in an effective amount and exhibit sufficient adhesion. Moreover, the adhesive layer with such a thickness can be readily formed.

The support is not particularly limited, and is preferably one substantially impermeable to the above ingredients. In other words, it is preferably one that prevents a decrease in the amounts of the antigen and the immunity induction promoting composition containing the immunity induction promoter whose active ingredient is an antimicrobial drug and other ingredients by not allowing them to pass through the support and escape from the back side.

The support may be a single film of polyester, polyamide, polyvinylidene chloride, polyethylene, polypropylene, polyvinyl chloride, ethylene-ethyl acrylate copolymer, polytetrafluoroethylene, ionomer resin, metal foil, or the like, or it may be a laminated film of these mentioned above. Preferred among these is a laminated film of a nonporous plastic film which is made of any of the above-mentioned materials and a porous film, in view of achieving good adhesiveness (anchoring properties) between the support and the adhesive layer. In this case, the adhesive layer is preferably formed on the porous film side.

Any porous film that improves the anchoring properties between the support and the adhesive layer may be used. Examples thereof include paper, woven fabrics, nonwoven fabrics, knitted fabrics, and mechanically perforated sheets. Preferred among these are paper, woven fabrics, and nonwoven fabrics, in view of factors such as handleability. A porous film having a thickness in the range of 1 to 200 μm is preferably employed in view of improving anchoring properties and also in view of factors such as flexibility and attachment operability of the tape. In addition, in the case where the porous film is a woven fabric or a nonwoven fabric, the weight per unit area is preferably 5 to 30 $g/m^2$, more preferably 6 to 15 $g/m^2$.

A suitable support is a laminated film of a polyester film (preferably, a polyethylene terephthalate film) having a thickness of 1.5 to 6 μm and a polyester (preferably, polyethylene terephthalate) nonwoven fabric having a weight per unit area of 6 to 15 $g/m^2$.

The release liner is not particularly limited as long as it is preliminarily subjected to release treatment and ensures sufficiently light releasability. Examples thereof include films made of polyester, polyvinyl chloride, polyvinylidene chloride, polyethylene terephthalate, or the like; paper such as wood-free paper and glassine paper; and laminate films of wood-free paper or glassine paper and polyolefin, which are preliminarily treated to be releasable by applying, for example, silicone resin or fluorine resin to the surface to be in contact with the adhesive layer.

The thickness of the release liner is preferably 10 to 200 μm, more preferably 25 to 100 μm.

The release liner is preferably formed from polyester (in particular, polyethylene terephthalate) resin in view of factors such as barrier and cost. In this case, the thickness of the release liner is preferably about 25 to 100 μm in view of handleability.

<Vaccine Pharmaceutical Composition for Transmucosal Administration>

Examples of transmucosal administration include sublingual administration, transnasal administration, buccal administration, rectal administration, and vaginal administration.

The dosage form of the vaccine pharmaceutical composition for transmucosal administration may be, for example, a semisolid formulation such as a gel (jelly), a cream, an ointment, or a plaster; a solution; a solid formulation such as a powder, a fine granule, a granule, a film, a tablet, or an orally disintegrating tablet; a mucosal spray formulation such as an aerosol; or an inhalant. Categories, definitions, properties, production processes, and the like of these formulations are well known in the relevant art. For example, see the Japanese Pharmacopoeia, 16th Edition. Any known material may be used for these formulations.

The amounts of the antigen and the immunity induction promoting composition containing the immunity induction promoter whose active ingredient is an antimicrobial in the vaccine pharmaceutical composition for transmucosal administration are not particularly limited. The amount of the antigen is preferably 0.01 to 40% by weight, more preferably 0.1 to 30% by weight. The amount of the immunity induction promoter whose active ingredient is an antimicrobial is preferably 0.001 to 30% by weight, more preferably 0.01 to 20% by weight.

<Vaccine Pharmaceutical Composition for Intradermal, Subcutaneous, or Intramuscular Administration>

The dosage form of the vaccine pharmaceutical composition for intradermal, subcutaneous, or intramuscular administration is an injectable form with a certain level of fluidity, and may be, for example a solution, a water-soluble or hydrophobic suspension, or a cream. Categories, definitions, properties, production processes, and the like of these formulations are well known in the relevant art. For example, see the Japanese Pharmacopoeia, 16th Edition. Any known material may be used for these formulations.

The amounts of the antigen and the immunity induction promoting composition containing the immunity induction promoter whose active ingredient is an antimicrobial in the vaccine pharmaceutical composition for intradermal, subcutaneous, or intramuscular administration are not particularly limited. The amount of the antigen is preferably 0.01 to 40% by weight, more preferably 0.1 to 30% by weight. The amount of the immunity induction promoter whose active ingredient is an antimicrobial is preferably 0.001 to 30% by weight, more preferably 0.01 to 20% by weight.

The vaccine pharmaceutical composition of the present invention may optionally contain additive(s). The additive(s) are used in accordance with the main component of the base, compatibility with the antigen and the immunity induction-promoting composition containing the immunity induction promoter whose active ingredient is an antimicrobial drug, and the intended administration regimen. Examples thereof include tonicity agents, antiseptic bactericides, antioxidants, solubilizers, solubilizer aids, suspending agents, fillers, pH adjusters, stabilizers, absorption promoters, release rate controlling agents, colorants, plasticizers, crosslinking agents, and adhesives. These additives may be used alone or in combination of two or more thereof.

The adhesive layer may further contain a skin permeation enhancer.

As used herein, the term "salt" may refer to any organic or inorganic acid salt, and is preferably a pharmacologically acceptable salt.

As used herein, the term "pharmacologically acceptable salt" refers to a salt that does not have an adverse effect on the administration subject and does not eliminate the pharmacological activity of components of the composition. Examples thereof include inorganic acid salts (e.g., hydrochloride, phosphate), organic acid salts (e.g., acetate, phthalate, TFA salt), metal salts such as alkali metal salts (e.g., sodium salt, potassium salt), alkaline earth metal salts (e.g., calcium salt, magnesium salt) and aluminum salt, and amine salts (e.g., triethylamine salt, benzylamine salt, diethanolamine salt, t-butylamine salt, dicyclohexylamine salt, arginine salt, dimethyl ammonium salt, ammonium salt).

In administration of the vaccine pharmaceutical composition of the present invention to the subject, the therapeutically effective amount of the antigen may widely vary depending on the severity of the disease, age and relative health of the subject, and other known factors. Generally, satisfactory results can be obtained at a dose of about 0.1 μg to 1 g/kg body weight per day. The immunity induction-promoting composition containing an immunity induction promoter whose active ingredient is an antimicrobial drug is simultaneously or sequentially administered with the antigen. Simultaneous administration is preferred. The therapeutically effective amount of the immunity induction promoting composition containing the immunity induction promoter whose active ingredient is an antimicrobial drug may widely vary depending on the specific type of the immunity induction promoter used and the presence or absence of other cellular immunity induction promoter(s). Generally, satisfactory results can be obtained at about 0.01 μg to 1 g/kg body weight per day.

The daily dose may be administered in one time, or may be split into multiple doses (i.e., two or more doses, for example, 2, 3, 4, or 5 doses). Preferably, the period of continuous administration per dose is appropriately determined in the range from 1 minute to 7 days. Preferably, the administration interval is appropriately selected from once a day to once a year (for example, once a day, once every 2 days, once every 3 days, once a week, once every 2 weeks, once a month, once every 3 months, once every 6 months, once a year, etc.), or longer administration intervals, depending on the condition of patients, severity of the disease, and whether it is for therapeutic purposes or preventive purposes. Generally, for the therapeutic purposes for a patient actually having a severe disease, the vaccine pharmaceutical composition of the present invention is preferably administered at a higher frequency and/or in a higher dose, while for the preventive purposes for patients not having a disease, the vaccine pharmaceutical composition of the present invention is preferably administered at a lower frequency and/or in a lower dose.

Advantageous Effects of Invention

The present invention enables safe and effective induction of cellular immunity against an antigen since the immunity induction-promoting composition used contains an immunity induction promoter whose active ingredient is an antimicrobial drug having an enough accumulated track record of use as a medicine.

In cases where the vaccine pharmaceutical composition of the present invention is administered to a body surface, the vaccine pharmaceutical composition can be noninvasively (e.g., transdermally or transmucosally) administered, leading to excellent compliance. In other words, the problems concerning QOL of patients can be reduced, such as pain, fear, injection scars and scarring thereof, and the burden of visiting the hospital in their daily life when repeated administration is required. In addition, patients can perform administration by themselves as the administration is easy, which allows medical practitioners to avoid the risk of infection due to needle pricking. Moreover, the medical waste which require special disposition, such as injection needles, are not generated.

In the case of the vaccine pharmaceutical composition of the present invention in the form of a patch such as a tape or a poultice, it is advantageous in that a predetermined dose can be reliably administered; the drug release rate can be controlled at any rate; and the drug is prevented from being attached to a site other than the intended site. In addition, since a patch is easily detachable, it is advantageous in that patients can immediately discontinue administration on their own by removing the patch from the site of application when an adverse effect occurs, for example.

Administration of the vaccine pharmaceutical composition of the present invention gives a significantly improved cellular immunity-inducing effect compared with administration of the antigen alone. The use of the vaccine pharmaceutical composition of the present invention for non-invasive administration to the body surface (e.g., transdermal administration or transmucosal administration) can induce stronger immunity than administration by injection.

DESCRIPTION OF EMBODIMENTS

Figure 1:
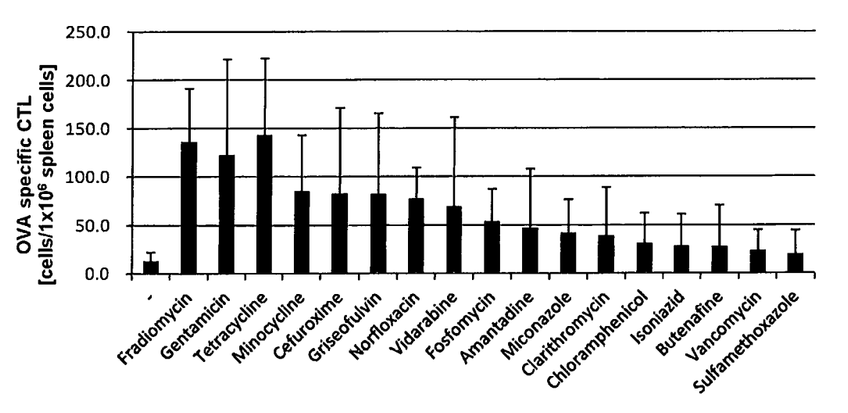
FIG. 1 shows a cellular immunity-inducing effect when creams for transdermal administration obtained in examples and comparative examples are transdermally administered.

The present invention is described specifically in detail in the following with reference to, but not limited to, examples.

Examples 1 to 17, Comparative Example 1

(Preparation of Creams for Transdermal Administration)

Creams for transdermal administration having a composition as shown in Table 1 below were prepared. Specifically, an antigen (peptide or protein), an immunity induction promoter whose active ingredient is an antimicrobial drug, a helper peptide, and 15% by weight of dimethylsulfoxide (DMSO) were mixed in amounts specified in Table 1. To the resulting mixture was added a base (base cream) to a total weight of 100% by weight, followed by mixing to give a cream for transdermal administration. The base cream used was prepared by mixing materials shown in Table 2 in amounts as specified. White Vaseline, sorbitan monostearate, isostearic acid, benzyl alcohol, stearyl alcohol, polysorbate 60, concentrated glycerin, and dimethylsulfoxide (DMSO) were purchased from Wako Pure Chemical Industries, Ltd. Cetanol was purchased from Tokyo Chemical Industry Co., Ltd.

A PET film/PET nonwoven fabric laminate (area: 0.7 $cm^2$) was attached to the center of an adhesive tape for fixing in such a manner that the PET film was in contact with the tape, thereby preparing a complex base. To a nonwoven fabric portion of the obtained complex base, 4 mg of the cream was applied. This was used as an administration sample in an immunity test.

(Immunity Induction Promoter Whose Active Ingredient is Antimicrobial Drug)
Fradiomycin (Wako Pure Chemical Industries, Ltd.)
Gentamicin (Wako Pure Chemical Industries, Ltd.)
Tetracycline (Wako Pure Chemical Industries, Ltd.)
Minocycline (Wako Pure Chemical Industries, Ltd.)
Cefuroxime (Wako Pure Chemical Industries, Ltd.)
Griseofulvin (Wako Pure Chemical Industries, Ltd.)
Norfloxacin (Wako Pure Chemical Industries, Ltd.)
Vidarabine (Wako Pure Chemical Industries, Ltd.)
Fosfomycin (Wako Pure Chemical Industries, Ltd.)
Amantadine (Wako Pure Chemical Industries, Ltd.)
Miconazole (Wako Pure Chemical Industries, Ltd.)
Clarithromycin (Wako Pure Chemical Industries, Ltd.)
Chloramphenicol (Wako Pure Chemical Industries, Ltd.)
Isoniazid (Wako Pure Chemical Industries, Ltd.)
Butenafine (Wako Pure Chemical Industries, Ltd.)
Vancomycin (Wako Pure Chemical Industries, Ltd.)
Sulfamethoxazole (Wako Pure Chemical Industries, Ltd.)

(Antigenic Peptide)
OVAp (OVA peptide, 8-amino acid peptide having the sequence Ser Ile Ile Asn Phe Glu Lys Leu (SEQ ID No. 15))

<Evaluation>

The creams for transdermal administration obtained in the examples and comparative examples were evaluated as follows.

(Evaluation on Cellular Immunity-Inducing Effect)

According to the procedure described below, the cream for transdermal administration was used to carry out a mouse immunity test using an animal model for immunological evaluation. Subsequently, the level of induction of antigen-specific cellular immunity was evaluated by ELISPOT assay.

(1) Animal Model for Immunological Evaluation

The "animal model for immunological evaluation" herein refers to an animal model for evaluating the immunity-inducing properties of a vaccine pharmaceutical composition (in the present case, a cream for transdermal administration), and specifically refers to an animal model for evaluating the level of the cellular immunity induced by the cream for transdermal administration.

In consideration of the compatibility between the antigen in the cream for transdermal administration and MHC class I molecules of the animal, the animal model used for immunological evaluation was an animal with which induction of the cellular immunity by the antigen in the cream for transdermal administration can be evaluated.

(2) Mouse Immunity Test of Creams for Transdermal Administration

According to Table 1, a mouse was provided and its back was shaved. After a certain rearing period for recovery from skin damage caused by the shaving, 4 mg of the cream for transdermal administration was administered to the skin of the back for 24 hours and then removed therefrom. The mouse was reared for six days. Six days after the administration, the spleen was extracted, and a spleen cell suspension was prepared. Spleen cells ($1 \times 10^6$ cells/well) and an antigen peptide (100 μM) or antigen protein (100 μg/mL) together with a culture fluid were poured into wells of an ELISPOT plate on which an anti-mouse IFN-γ antibody was immobilized, and co-cultured under the culture conditions of 37° C. and 5% CO2 for 20 hours. The number of IFN-γ-producing cell spots (the number of spots/$1 \times 10^6$ cells) was evaluated by the ELISPOT assay. Table 1 shows the number of IFN-γ-producing cell spots as the "Immunity result".

[Table 1]

TABLE 1

| | Administration route | Dosage form | Dose [mg] | Antigen | | Antimicrobial | |
| | | | | Name | Amount [%] | Name | Function |
| --- | --- | --- | --- | --- | --- | --- | --- |
| Comparative Example 1 | Transdermal | cream | 4 | OVAp | 5 | — | |
| Example 1 | Transdermal | cream | 4 | OVAp | 5 | Fradiomycin | Bacterial protein synthesis inhibition (30S ribosome-binding type) |
| Example 2 | Transdermal | cream | 4 | OVAp | 5 | Gentamicin | Bacterial protein synthesis inhibition (30S ribosome-binding type) |
| Example 3 | Transdermal | cream | 4 | OVAp | 5 | Tetracycline | Bacterial protein synthesis inhibition (30S ribosome-binding type) |
| Example 4 | Transdermal | cream | 4 | OVAp | 5 | Minocycline | Bacterial protein synthesis inhibition (30S ribosome-binding type) |
| Example 5 | Transdermal | cream | 4 | OVAp | 5 | Cefuroxime | Bacterial cell wall synthesis inhibition |
| Example 6 | Transdermal | cream | 4 | OVAp | 5 | Griseofulvin | Antifungal activity |
| Example 7 | Transdermal | cream | 4 | OVAp | 5 | Norfloxacin | Bacterial nucleic acid synthesis |
| Example 8 | Transdermal | cream | 4 | OVAp | 5 | Vidarabine | Antiviral activity |
| Example 9 | Transdermal | cream | 4 | OVAp | 5 | Fosfomycin | Bacterial cell wall synthesis inhibition |

TABLE 1-continued

| | | | | | | | |
|---|---|---|---|---|---|---|---|
| Example 10 | Transdermal | cream | 4 | OVAp | 5 | Amantadine | Antiviral activity |
| Example 11 | Transdermal | cream | 4 | OVAp | 5 | Miconazole | Antifungal activity |
| Example 12 | Transdermal | cream | 4 | OVAp | 5 | Clarithromycin | Bacterial protein synthesis inhibition (50S ribosome-binding type) |
| Example 13 | Transdermal | cream | 4 | OVAp | 5 | Chloramphenicol | Bacterial protein synthesis inhibition (50S ribosome-binding type) |
| Example 14 | Transdermal | cream | 4 | OVAp | 5 | Isoniazid | Bacterial cell wall synthesis inhibition |
| Example 15 | Transdermal | cream | 4 | OVAp | 5 | Butenafine | Antifungal activity |
| Example 16 | Transdermal | cream | 4 | OVAp | 5 | Vancomycin | Bacterial cell wall synthesis inhibition |
| Example 17 | Transdermal | cream | 4 | OVAp | 5 | Sulfamethoxazole | Bacteria nucleic acid synthes s inhibition |

| | Antimicrobial | | Helper peptide | | Immunity | Immunity |
|---|---|---|---|---|---|---|
| | Structure | Amount [%] | Name | Amount [%] | evaluation mouse | result (ELISPOT) |
| Comparative Example 1 | | — | PEP | 1 | C57/BL6 | 13 |
| Example 1 | Aminoglycoside skeleton | 3 | PEP | 1 | C57/BL6 | 136 |
| Example 2 | Aminoglycoside skeleton | 3 | PEP | 1 | C57/BL6 | 122 |
| Example 3 | Tetracycline skeleton | 3 | PEP | 1 | C57/BL6 | 143 |
| Example 4 | Tetracycline skeleton | 3 | PEP | 1 | C57/BL6 | 85 |
| Example 5 | β-lactam skeleton | 3 | PEP | 1 | C57/BL6 | 82 |
| Example 6 | Griseofulvin skeleton | 3 | PEP | 1 | C57/BL6 | 82 |
| Example 7 | Quinolone skeleton | 3 | PEP | 1 | C57/BL6 | 78 |
| Example 8 | Purine skeleton | 3 | PEP | 1 | C57/BL6 | 70 |
| Example 9 | Fosfomycin skeleton | 3 | PEP | 1 | C57/BL6 | 54 |
| Example 10 | Adamantane skeleton | 3 | PEP | 1 | C57/BL6 | 47 |
| Example 11 | Azole skeleton | 3 | PEP | 1 | C57/BL6 | 42 |
| Example 12 | Macrolide skeleton | 3 | PEP | 1 | C57/BL6 | 39 |
| Example 13 | Amphenicol skeleton | 3 | PEP | 1 | C57/BL6 | 31 |
| Example 14 | Isonicotinic acid skeleton | 3 | PEP | 1 | C57/BL6 | 28 |
| Example 15 | Benzylamine skeleton | 3 | PEP | 1 | C57/BL6 | 28 |
| Example 16 | Glycopeptide skeleton | 3 | PEP | 1 | C57/BL6 | 23 |
| Example 17 | Aminosalicylic acid skeletor | 3 | PEP | 1 | C57/BL6 | 20 |

PEP = Peptide-25

TABLE 2

| Additive | Amount [% by weight] |
|---|---|
| White Vaseline | 60.7 |
| Sorbitan monostearate | 0.7 |
| Isostearic acid | 12.0 |
| Benzyl alcohol | 2.4 |
| Cetanol | 2.4 |
| Stearyl alcohol | 3.5 |
| Polysorbate 60 | 3.5 |
| Concentrated glycerin | 2.4 |
| Purified water | 12.4 |

As shown in FIG. 1, containing the immunity induction promoters whose active ingredient is an antimicrobial drug shown in Examples 1 to 17, administration of the creams for transdermal administration more strongly induced cellular immunity than transdermal administration of an antigen alone.

INDUSTRIAL APPLICABILITY

The immunity induction-promoting composition and vaccine pharmaceutical composition of the present invention contain an immunity induction promoter whose active ingredient is an antimicrobial drug that already has an enough accumulated track record of use as a medicine. The immunity induction-promoting composition and vaccine pharmaceutical composition are thus capable of safely and effectively inducing cellular immunity against various antigens, thus exhibiting a high cellular immunity-inducing effect.

The invention claimed is:

1. A vaccine pharmaceutical composition for immunity induction comprising:
   an antigen;
   an immunity induction-promoting composition comprising an antimicrobial drug; and
   a helper peptide,
   wherein
   the antimicrobial drug is at least one selected from a compound that has antifungal activity and a compound that has antiviral activity; and
   the compound that has antifungal activity has a griseofulvin skeleton and/or an azole skeleton, and
   the compound that has antiviral activity has a purine skeleton and/or an adamantane skeleton.

2. The vaccine pharmaceutical composition for immunity induction according to claim 1,
   wherein
   the compound having a griseofulvin skeleton is griseofulvin,
   the compound having an azole skeleton is miconazole,
   the compound having a purine skeleton is vidarabine, and
   the compound having an adamantane skeleton is amantadine.

3. The vaccine pharmaceutical composition for immunity induction according to claim 1, wherein the helper peptide is selected from Peptide-25, Peptide-25B, and PADRE.

4. The vaccine pharmaceutical composition for immunity induction according to claim 2, wherein the helper peptide is selected from Peptide-25, Peptide-25B, and PADRE.

* * * * *

SEQUENCE LISTING

```
<160> NUMBER OF SEQ ID NOS: 15

<210> SEQ ID NO 1
<211> LENGTH: 9
<212> TYPE: PRT
<213> ORGANISM: Homo sapiens

<400> SEQUENCE: 1

Ala Tyr Ala Cys Asn Thr Ser Thr Leu
1               5

<210> SEQ ID NO 2
<211> LENGTH: 9
<212> TYPE: PRT
```

```
<213> ORGANISM: Homo sapiens

<400> SEQUENCE: 2

Glu Tyr Ile Leu Ser Leu Glu Glu Leu
1               5

<210> SEQ ID NO 3
<211> LENGTH: 9
<212> TYPE: PRT
<213> ORGANISM: Homo sapiens

<400> SEQUENCE: 3

Thr Tyr Leu Pro Thr Asn Ala Ser Leu
1               5

<210> SEQ ID NO 4
<211> LENGTH: 9
<212> TYPE: PRT
<213> ORGANISM: Homo sapiens

<400> SEQUENCE: 4

Ile Met Pro Lys Ala Gly Leu Leu Ile
1               5

<210> SEQ ID NO 5
<211> LENGTH: 9
<212> TYPE: PRT
<213> ORGANISM: Homo sapiens

<400> SEQUENCE: 5

Val Leu Gln Glu Leu Asn Val Thr Val
1               5

<210> SEQ ID NO 6
<211> LENGTH: 9
<212> TYPE: PRT
<213> ORGANISM: Homo sapiens

<400> SEQUENCE: 6

Lys Val Phe Gly Ser Leu Ala Phe Val
1               5

<210> SEQ ID NO 7
<211> LENGTH: 9
<212> TYPE: PRT
<213> ORGANISM: Homo sapiens

<400> SEQUENCE: 7

Lys Val Ala Glu Ile Val His Phe Leu
1               5

<210> SEQ ID NO 8
<211> LENGTH: 9
<212> TYPE: PRT
<213> ORGANISM: Homo sapiens

<400> SEQUENCE: 8

Lys Ile Phe Gly Ser Leu Ala Phe Leu
1               5

<210> SEQ ID NO 9
<211> LENGTH: 9
<212> TYPE: PRT
<213> ORGANISM: Homo sapiens
```

```
<400> SEQUENCE: 9

Ser Thr Ala Pro Pro Val His Asn Val
1               5

<210> SEQ ID NO 10
<211> LENGTH: 9
<212> TYPE: PRT
<213> ORGANISM: Hepatitis C virus

<400> SEQUENCE: 10

Asp Leu Met Gly Tyr Ile Pro Ala Val
1               5

<210> SEQ ID NO 11
<211> LENGTH: 9
<212> TYPE: PRT
<213> ORGANISM: Hepatitis B virus

<400> SEQUENCE: 11

Trp Leu Ser Leu Leu Val Pro Phe Val
1               5

<210> SEQ ID NO 12
<211> LENGTH: 15
<212> TYPE: PRT
<213> ORGANISM: Mycobacterium tuberculosis

<400> SEQUENCE: 12

Phe Gln Asp Ala Tyr Asn Ala Ala Gly Gly His Asn Ala Val Phe
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Peptide-25B

<400> SEQUENCE: 13

Phe Gln Asp Ala Tyr Asn Ala Val His Ala Ala His Ala Val Phe
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: PADRE
<220> FEATURE:
<221> NAME/KEY: MOD_RES
<222> LOCATION: (1)..(1)
<223> OTHER INFORMATION: D-alanine
<220> FEATURE:
<221> NAME/KEY: MOD_RES
<222> LOCATION: (3)..(3)
<223> OTHER INFORMATION: cyclohexylalanine
<220> FEATURE:
<221> NAME/KEY: MOD_RES
<222> LOCATION: (13)..(13)
<223> OTHER INFORMATION: D-alanine

<400> SEQUENCE: 14

Ala Lys Ala Val Ala Ala Trp Thr Leu Lys Ala Ala Ala
1               5                   10

<210> SEQ ID NO 15
<211> LENGTH: 8
```

```
<212> TYPE: PRT
<213> ORGANISM: Gallus gallus

<400> SEQUENCE: 15

Ser Ile Ile Asn Phe Glu Lys Leu
1               5
```